US012159703B2

(12) United States Patent
Spooner et al.

(10) Patent No.: US 12,159,703 B2
(45) Date of Patent: Dec. 3, 2024

(54) SMARTWATCH THERAPY APPLICATION

(71) Applicant: Zimmer US, Inc., Warsaw, IN (US)

(72) Inventors: Ted Spooner, Grand Rapids, MI (US); Richard Wells, Ada, MI (US); Travis Dittmer, Grand Rapids, MI (US); Timothy R. Price, East Grand Rapids, MI (US); Kshitij Agarwal, Grand Rapids, MI (US)

(73) Assignee: Zimmer US, Inc., Warsaw, IN (US)

(*) Notice: Subject to any disclaimer, the term of this patent is extended or adjusted under 35 U.S.C. 154(b) by 307 days.

(21) Appl. No.: 15/917,065

(22) Filed: Mar. 9, 2018

(65) Prior Publication Data

US 2018/0261316 A1  Sep. 13, 2018

Related U.S. Application Data

(60) Provisional application No. 62/469,792, filed on Mar. 10, 2017.

(51) Int. Cl.
G16H 20/30 (2018.01)
A61B 5/00 (2006.01)
(Continued)

(52) U.S. Cl.
CPC ............ *G16H 20/30* (2018.01); *A61B 5/681* (2013.01); *A61B 5/7465* (2013.01); *H04M 1/72412* (2021.01); *A63B 71/0622* (2013.01)

(58) Field of Classification Search
CPC . G06F 19/3481; G06F 19/3418; G16H 20/30; G16H 40/67; G16H 50/20;
(Continued)

(56) References Cited

U.S. PATENT DOCUMENTS 9,939,784 B1* 4/2018 Berardinelli ...... H04M 1/72412
10,216,904 B2  2/2019 Hughes et al.
(Continued)

FOREIGN PATENT DOCUMENTS

CN 106469250 A 3/2017
CN 110419081 A 11/2019
(Continued)

OTHER PUBLICATIONS

"International Application Serial No. PCT US2018 021762, International Search Report mailed Jun. 8, 2018", 5 pgs.
(Continued)

Primary Examiner — Jack Yip
(74) Attorney, Agent, or Firm — Schwegman Lundberg & Woessner, P.A.

(57) ABSTRACT

Systems and methods may use a mobile device communicatively coupled to a wearable device to present an exercise to a user. The systems and methods may modify a therapy calendar, for example, based on information determined from the exercise (e.g., repetitions completed, a duration completed, video, etc.), feedback from the user, or the like. A method may include receiving a control command from a wearable device communicatively coupled to a mobile device, the control command causing an action to be taken by the mobile device related to the exercise. The therapy calendar may be automatically modified, such as in response to determining a number of repetitions or a duration of an exercise. The modified therapy calendar may be presented on a user interface, such as on a display of the wearable device or the mobile device.

20 Claims, 12 Drawing Sheets

(51) Int. Cl.
*H04M 1/72412* (2021.01)
*A63B 71/06* (2006.01)

(58) Field of Classification Search
CPC ............ A63B 24/0062; A63B 24/0075; A63B 71/0622; A61B 5/1118; A61B 5/0022; A61B 5/486; A61B 5/681; A61B 5/7465; G09B 19/0038; G09B 19/003; H04M 1/72412

See application file for complete search history.

(56) References Cited

U.S. PATENT DOCUMENTS

| | | | | |
|---|---|---|---|---|
| 2012/0258433 | A1* | 10/2012 | Hope | G16H 20/30 434/247 |
| 2014/0132410 | A1* | 5/2014 | Chang | G06F 3/014 340/539.11 |
| 2014/0371887 | A1* | 12/2014 | Hoffman | A61B 5/1118 700/91 |
| 2015/0088536 | A1 | 3/2015 | Thelen et al. | |
| 2015/0134088 | A1 | 5/2015 | Romeo et al. | |
| 2015/0199494 | A1* | 7/2015 | Koduri | G16H 20/30 700/91 |
| 2015/0286285 | A1* | 10/2015 | Pantelopoulos | G06F 3/048 345/156 |
| 2016/0048189 | A1* | 2/2016 | Bhardwaj | G06F 1/3206 713/320 |
| 2016/0086500 | A1* | 3/2016 | Kaleal, III | G06Q 10/10 434/257 |
| 2016/0198322 | A1* | 7/2016 | Pitis | H04W 4/80 455/420 |
| 2016/0220175 | A1 | 8/2016 | Tam et al. | |
| 2017/0053542 | A1* | 2/2017 | Wilson | G09B 5/02 |
| 2017/0329933 | A1* | 11/2017 | Brust | G06F 16/252 |
| 2017/0368413 | A1* | 12/2017 | Shavit | A63B 24/0075 |
| 2018/0140900 | A1* | 5/2018 | Kim | A63B 24/0075 |
| 2018/0181722 | A1* | 6/2018 | Boland | G16H 50/20 |
| 2019/0066832 | A1* | 2/2019 | Kang | A61B 5/4884 |

FOREIGN PATENT DOCUMENTS

| | | |
|---|---|---|
| EP | 3131027 | 2/2017 |
| WO | 2015108700 | 7/2015 |
| WO | WO-2018165560 A1 | 9/2018 |

OTHER PUBLICATIONS

"International Application Serial No. PCT US2018 021762, Written Opinion mailed Jun. 8, 2018", 12 pgs.

"European Application Serial No. 18713524.9, Response to Communication pursuant to Rules 161(1) and 162 EPC filed May 4, 2020", 29 pgs.

"European Application Serial No. 18713524.9, Response filed Jul. 31, 2023 to Communication Pursuant to Article 94(3) EPC mailed Mar. 22, 2023", 23 pgs.

"Chinese Application Serial No. 201880017107.3, Office Action mailed Nov. 23, 2022", w/ English Translation, 29 pgs.

"Chinese Application Serial No. 201880017107.3, Response filed Feb. 10, 2023 to Office Action mailed Nov. 23, 2022", w/ English claims, 14 pgs.

"European Application Serial No. 18713524.9, Communication Pursuant to Article 94(3) EPC mailed Mar. 22, 2023", 7 pgs.

* cited by examiner

SMARTWATCH THERAPY APPLICATION

CLAIM OF PRIORITY

This application claims the benefit of priority to U.S. Provisional Application Ser. No. 62/469,792, filed Mar. 10, 2017, titled "Smartwatch Therapy Application" which is hereby incorporated herein by reference in its entirety.

BACKGROUND

Occupational or physical therapy includes exercises or activities to recover from an injury, surgery, or to otherwise improve mobility. Often, patients fail to complete activities associated with rehabilitation. Typically, patients must go into a physical office of a therapist to interact and perform physical therapy, which is inconvenient for the patient and sometimes results in missed sessions or lack of follow up. Postoperative therapy is important and used to continue a patient's recovery. Failure to make an appointment, or difficulty due to pain or confusion may lead to further missed appointments or frustration by the patient resulting in not continuing the postoperative therapy. Similar concerns arise in the realm of "prehab," or prehabilitation. Furthermore, preoperative methods of providing educational content prior to surgery are lacking in the level of engagement they inspire in the end user and are inconvenient. Care teams also have poor visibility into patient adherence to prescribed prehab or therapy and are unable to track what educational items patients have completed or how the patients are feeling post surgery.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods for presenting and tracking pre and post-operative educational content and therapy, as well as collecting patient outcomes, are described herein. FIGS. 1-6 illustrate example mobile devices and example wearable devices displaying various aspects of an interactive therapy program in accordance with some embodiments.

The interactive therapy program may be associated with an upcoming or past surgical procedure. The interactive therapy program may include a complete calendar of events to prepare a patient for the surgery (preoperative) and assist in recovery after the procedure (postoperatively). The therapy program may include educational content as well as physical activities to be engaged in by the patient. The interactive therapy program (or surgical care plan) may include an interactive calendar component that may be displayed on a wearable device or a mobile device of the patient. The interactive calendar component may display events and to-do items, such as educational content or exercises recommended for recovery. For example, the interactive calendar may include a count-down to the surgery day, include an appointment for the surgery day, and include a regiment of recovery activities. The calendar may also include links to recommended educational content, which may pre-operatively explain the procedure and what to expect in recovery and post-operatively may explain the recovery activities.

In an example, the surgical care plan may begin 30 days before surgery and ends 90 days after completion of the surgical procedure, with follow up questionnaires continuing for another year (or more). After the initial 90 days post-surgery, the patient may be marked as discharged in the system. After the specified duration for questionnaires (e.g. 1 to 5 years) the patient data may be archived and the patient marked as inactive in the system, but the patient may be reactivated and reenrolled in the system if a subsequent surgery is scheduled (e.g. hip instead of knee, the other knee, or a revision surgery).

A wearable device may include a watch, a device with a sensor, or another device that may be attached to the body of the patient in some manner (e.g., embedded in clothing or a shoe). A mobile device includes a phone, such as an iPhone or an Android-based device, or a tablet.

Figure 1:
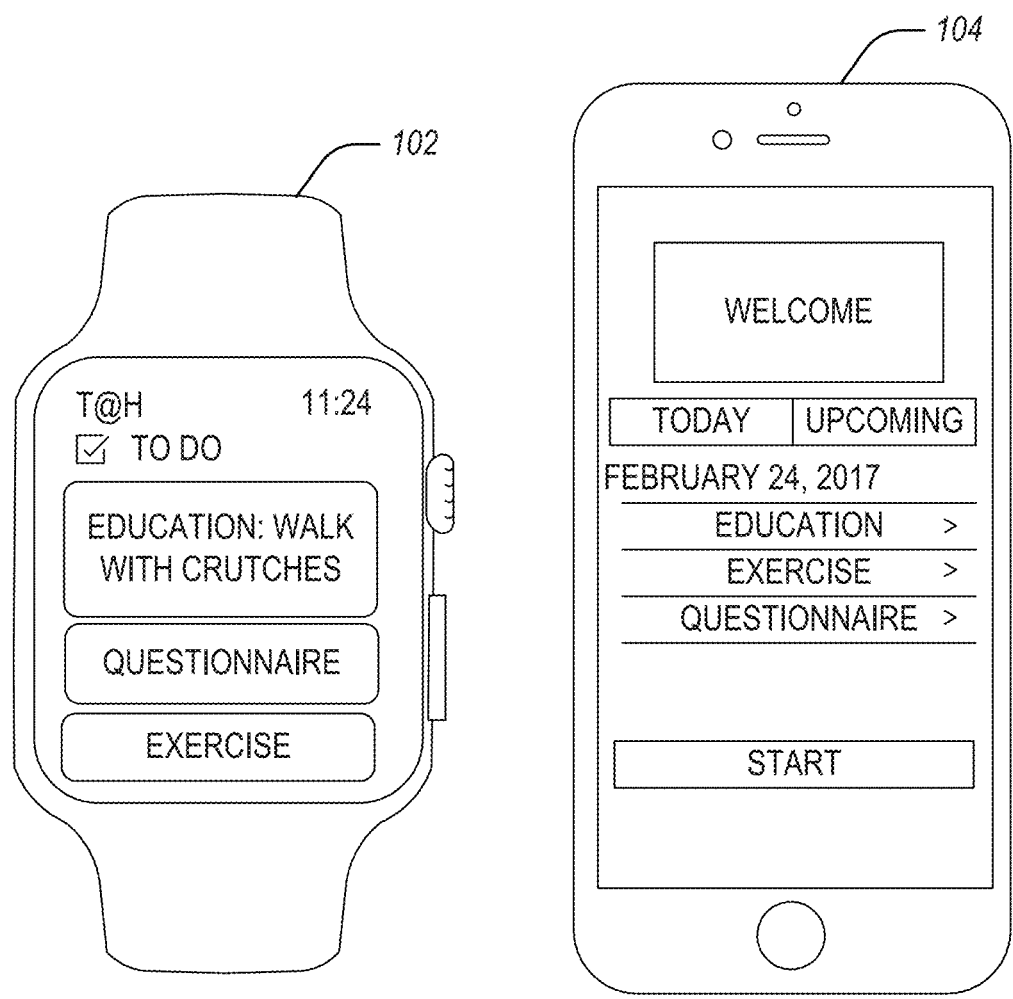
FIGS. 1-6 illustrate example mobile devices and example wearable devices displaying various aspects of a therapy program in accordance with some embodiments.
Figure 2:
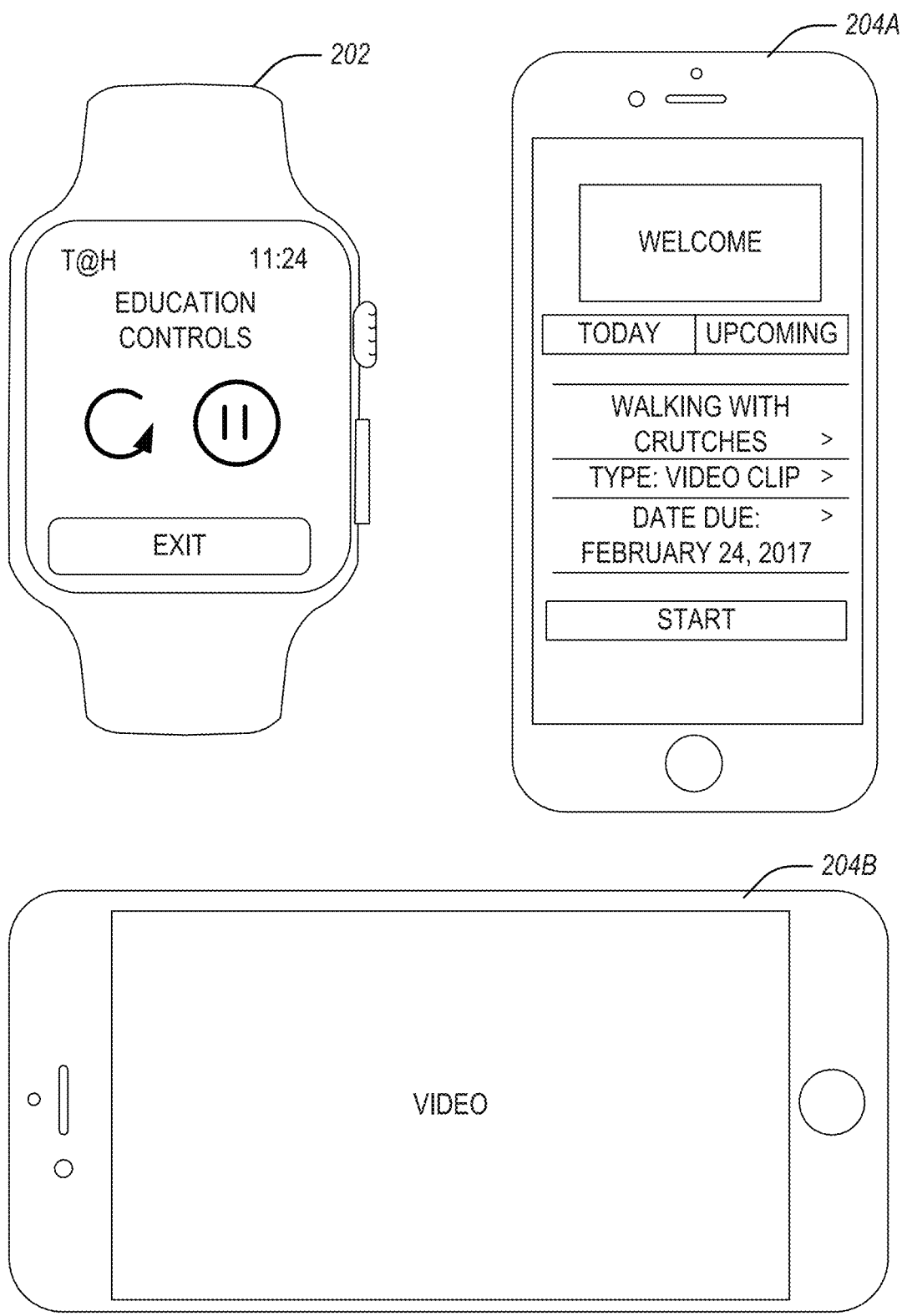

The therapy may include a number of tasks, which may be divided into categories, such as education, questionnaires, and routines. The tasks may be displayed on the mobile device 104 or the wearable device 102 in order, such as education then questionnaires, then routines. In another example, a patient or a therapist may select the order. The task displayed in FIG. 1 is an education task. Pressing the start button on the wearable device 102 activates a therapy video on the app (e.g., on the mobile device 104). The wearable device 102 may pause, restart, rewind, or finish the procedure. After finishing, the mobile device 104 may update server-side information, such as to report to a clinician or send a notification, and the server may maintain a database of the received reports. Adherence to the assigned or selected therapy program may be reported to the clinician, including details on the number of assigned educational tasks completed and the number of repetitions of exercise completed, along with user reported patient outcomes from the questionnaires or messaging to the care team. In certain examples, the term clinician may include the physician as well as various staff, such as an office administrator, a nurse navigator, and a scheduler. FIG. 2 illustrates a wearable device 202 controlling (e.g., with selectable indications for restarting or pausing an educational video) a mobile device with a first display 204A and a second display 204B. The first display 204A illustrates details (e.g., metadata) about the educational video to be shown. The second display 204B illustrates the educational video playing. Educational tasks may include other forms of content such as publications, instructions, diagrams, and quizzes.

Figure 3:
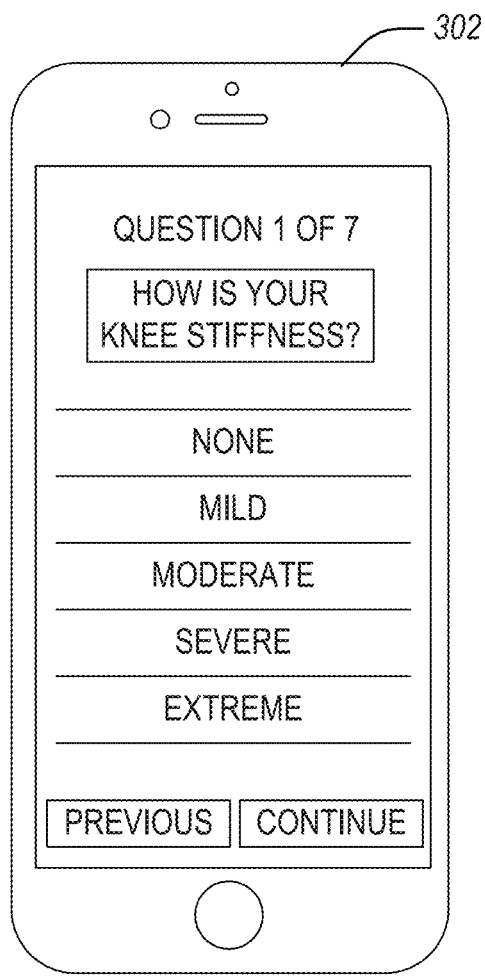

Then, after the education task is done a patient may perform a next task, which in the examples shown herein, is the questionnaires. The health questionnaire may include condition specific questions (e.g., hip replacement, total or partial knee replacement, shoulder replacement, etc.). In an example, the health questionnaire may include personalized issues (e.g., normal total knee replacement, but if the patient has diabetes, the questionnaire may ask an extra question or otherwise personalize). An example question is shown in FIG. 3 on mobile device 302.

Figure 4:
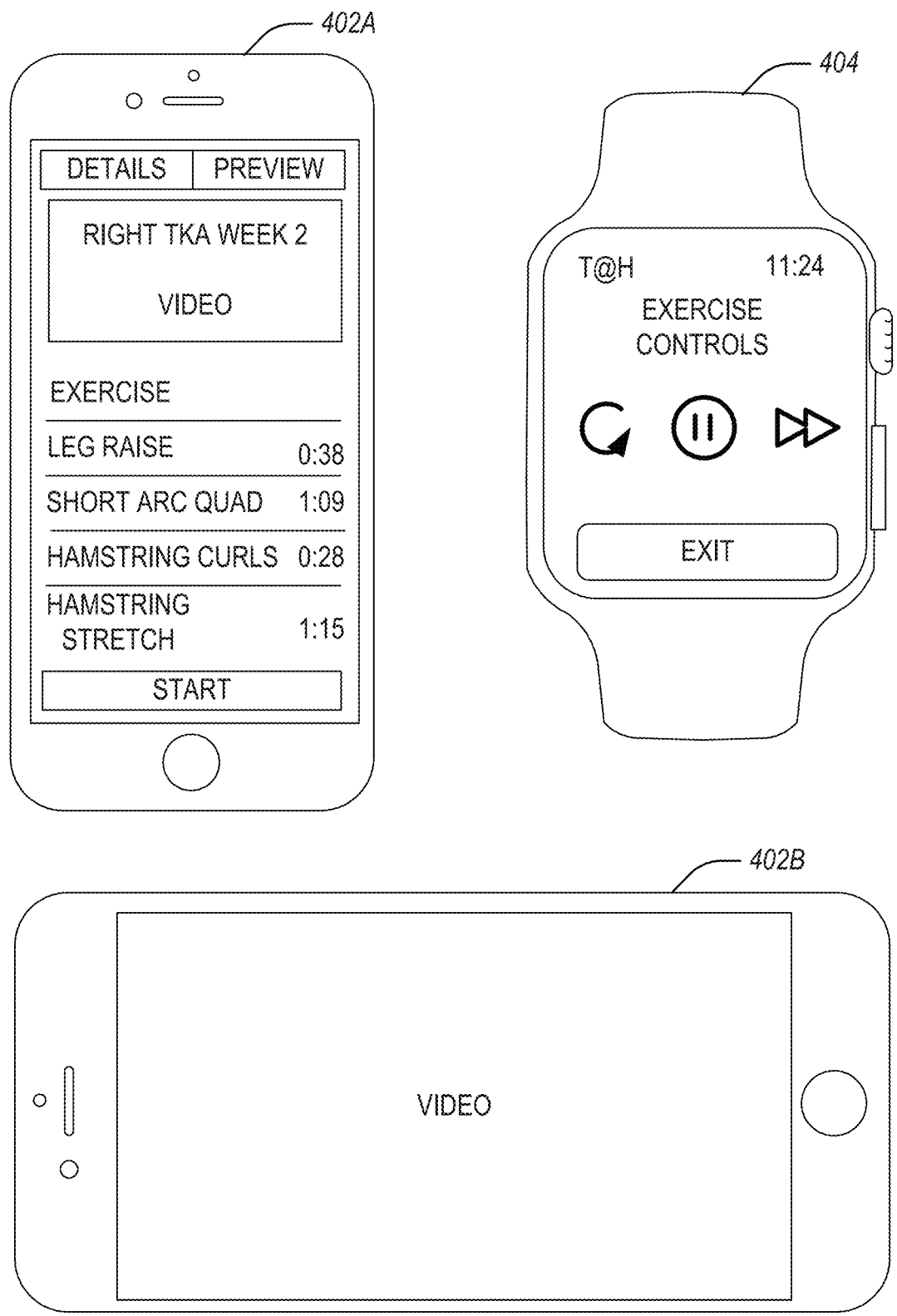

After the questionnaire is completed (or before if going in a different order), the routine task may be displayed and performed. The routine may be determined automatically, for example, based on where the patient is in a pre- or post-operative therapy calendar, or based on a therapist-selected or surgeon-selected plan. In an example, the wearable device 404 of FIG. 4 illustrates a displayed controller for restarting, pausing, or fast forwarding a routine shown on mobile device display 402B (with details about the routine shown on mobile device display 402A). The wearable device 404 may automatically track adherence to the routine or an adherence trajectory (e.g., the number of reps has not been met for the last three days, it is unlikely that tomorrow, the patient will hit the number of reps for that day). The tasks (e.g., the routine) may be automatically adjusted based on the adherence or adherence trajectory. The therapy changed as a result of the detection may include automatic or patient input issues, such as if the patient doesn't adhere to the routine, has or has reported worse pain, etc. The wearable device may also collect and report activity data in the background via onboard sensors in the wearable device (e.g., smartwatch) or in other connected devices (e.g., smartphone), for example flights of stairs climbed, total steps, heart rate. In an example, answers to the questionnaire (either prior to the routine or after, such as a following day questionnaire) may be used to evaluate adherence or change the suggested routine or individual exercises. In an example, AI or machine learning may be used to automatically change a therapy calendar (e.g., routines, reps, time, education, questionnaires, etc.). In another example, a doctor or therapist may be notified based on an issue traversing a threshold. For example, if the patient is unable to attain a certain percentage adherence to the recommended number of repetitions of a certain exercise, a notification may be generated and transmitted to the doctor, therapist, or an entire care team that has been associated with the patient in a configuration database on the server. Other issues that may cause or be used to change an exercise, routine, or calendar include insufficient duration of an exercise, incorrect form (e.g., when the patient is incapable or seems incapable of correct form), a missed or skipped exercise, etc. Adherence to form may be determined through analysis of sensor readings from accelerometers, gyroscopes, magnetometers and the like included with the wearable device, or through analysis of image/video recording of the patient in action (such as a recording captured by the camera on a phone or tablet playing the therapy video while the patient performs the repetitions shown by the video).

Figure 5:
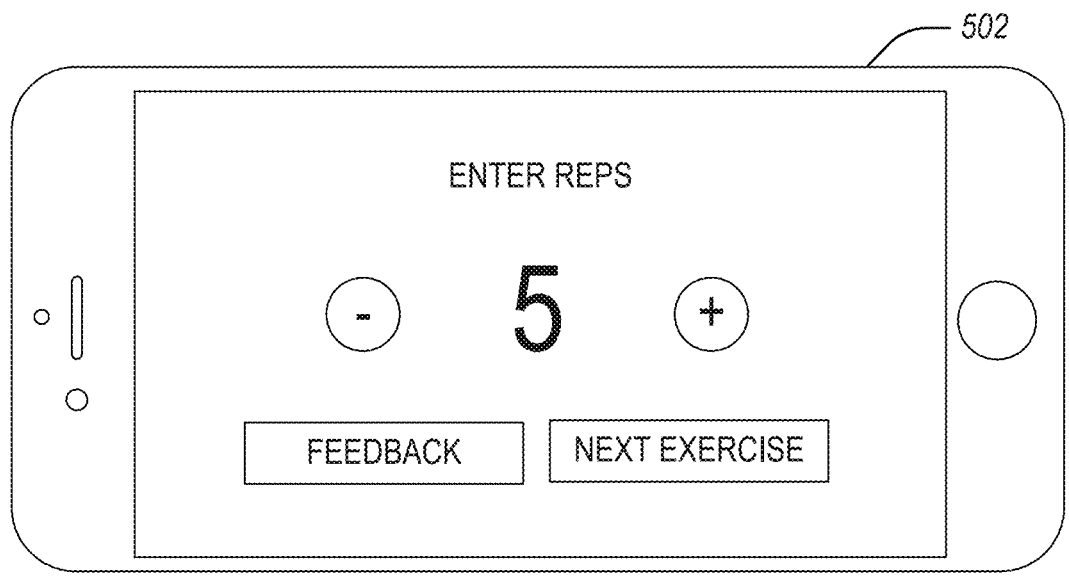
Figure 5:
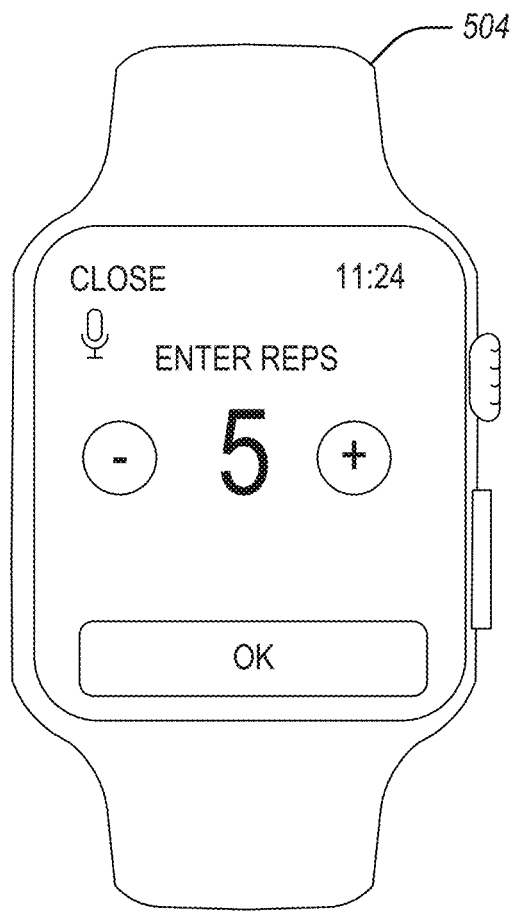

The patient may adjust the number of reps (e.g., automatically counted) using the wearable device 504 or the mobile device 502 of FIG. 5. For example, if the patient believes a rep was missed or over counted by the wearable device 504, the count may be adjusted via hard or soft controls on the wearable. Similarly, time doing a routine may be determined or changed. In an example, feedback may be generated using the mobile device 502. A next routine may be accessed using the wearable device 504 or the mobile device 502.

Figure 6:
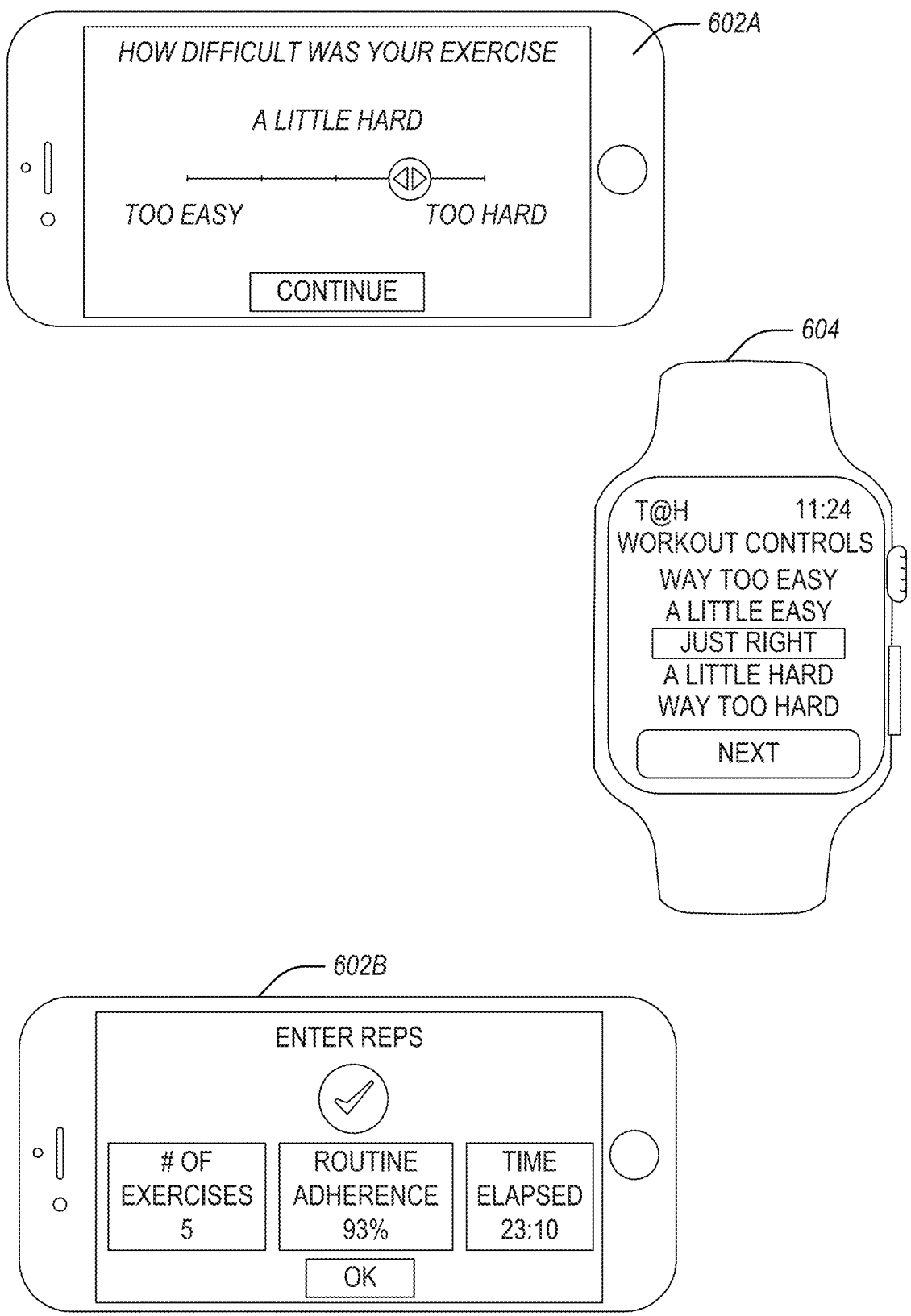

After a routine, education, and questionnaire (if any of these are on the task list and applicable) are completed, the patient may give feedback, such as a level of difficulty, a pain level, etc., which may be entered on the mobile device display 602A or the wearable device 604 of FIG. 6. A routine completion or task completion display 602B may be shown using the mobile device after completion of the routine or all tasks. The completion display 602B may include statistics or information automatically determined regarding the routine. The completion display 602B may also include an achievement badge or other recognition to the patient for the successful completion. The patient user may be presented with the option to share the achievement badge or completion statistics with contacts of his or her choosing (e.g., friends, family), via the application (to other users of the app), SMS/MMS, or email.

An example day's tasks may include:
1. Education: How To Walk With Your Crutches
2. Questionnaire: KOOS Jr.
3. Routine: Right TKA Week 2

In an example, to preview what to expect within each task, the name of the prescribed activity may be tapped. When the patient has completed a task, a green checkmark may appear to the right of its name. When all the patient's tasks have checkmarks next to them, the patient may be finished with the currently prescribed therapy (e.g., for the day). When new items are prescribed, a notification may be sent (e.g., to a mobile device or a wearable device). When a task is completed, a next task may automatically be displayed.

For the routine, after tapping start on the mobile device or on the routine on the wearable device, the app may navigate to a routine introduction screen that provides the patient with routine details or previews of the exercises prescribed. A safety or legal disclaimer may also be presented. The patient may tap start to begin routine on the mobile device or the wearable device. The mobile device or the wearable device may display a loading screen, a countdown to start screen to allow the patient time to get in position, or the like. When all the tasks for the day or time period are complete, an ending screen may be displayed.

A wearable device or a device otherwise coupled to a body may be used to count repetitions of an exercise, time an exercise, measure weight or resistance of an exercise, or the like. For example, if there is a wrist exercise, a wearable device on the wrist may automatically track the number of reps. The routine may automatically end or pause if the patient stops. A wearable device may be strapped or otherwise coupled to an ankle or knee to detect reps or time of an exercise using the knee. Other sensors or wearable devices may be attached to different body parts (or moved around) corresponding to a routine or exercise performed. For example, a local body network may be used, with sensors, such as an inertial measurement unit (IMU) or nine-axis sensor (e.g., including an accelerometer, a gyroscope, and a magnetometer), or other location, movement, or acceleration detecting sensor, placed on different body parts (e.g., knee, thigh, ankle, hip, etc.). The sensor or sensors may output sensor data, which may be used to determine success or overall health. The sensor data may be used to compare measurements or determinations of success to a model to determine where the patient is in relation to the model. Based on the comparison, a therapy calendar may be modified automatically. Thus, from automatically detected sensor data, the therapy calendar may be changed to accurately reflect a patient's progress and allow the patient to be more likely to succeed (e.g., according to the patient's personalized needs). In an example, a wearable device may be used to display a notification to or audibly notify a patient, such as by flashing an alert if the patient is moving the wrong leg for a routine, if the patient has completed the routine but is still doing an exercise, if the patient has poor form, etc. Wearable devices located at various locations on the patient's body may also provide haptic feedback to the user, for example an ankle-worn wearable may vibrate on a leg lift exercise if the patient did not lift his or her leg to the proper angle. The wearable device may also be used to determine if the patient has fallen while performing the routine and is not able to stand back up, in which case the mobile device may automatically call an emergency contact number saved on the device and or local emergency services. In certain examples, an emergency or support contact may be input into the preferences of the mobile device application, and this contact may be notified of any anomalies detected by the wearable device during a recovery period.

When a patient deviates or has a change to a therapy calendar (e.g., changes to tasks), a clinician may be notified, such as to warn of deviations, then the clinician may be presented with options for adjusting the plan. In certain examples, the nurse navigation may be the point of contact for such notifications, or some other staff person rather than the physician herself.

In an example, a wearable device may be used as a remote control for a mobile device camera (e.g., iOS Camera Remote app). This remote control may be used to record a video message to be sent to a provider (e.g., "This exercise hurts"). In another example, different types of assessments may be shown (e.g., am I doing this correctly). In yet another example, dialogue, such as addressing wound care, pictures of the wound, etc. may be sent or received by the patient to or from the therapist.

The therapist or clinician may use a desktop app (or mobile app) to communicate with the patient. A clinician dashboard may be used to alert the clinician to issues with the patient, provide suggestions, clinician may update the therapy plan, automatically and in real time that would get sent to the patient's app, etc. The clinician may receive or send video messages or pictures from or to the patient, and may also receive or forward messages to other members of the patient's assigned care team who are also users of the clinician-side application.

After surgery, the application may be used to request and collect information about the patient's disposition. For example, the application may track the scheduled date of surgery and receive automatic updates from the clinician or surgeon's scheduling system regarding changes to the surgical date. After the day of the scheduled surgery comes to pass, the application may request that the user provide disposition information (e.g., outpatient, in the hospital, in skilled nursing facility, or at home) on a daily basis until the patient reports he or she is at home. Disposition information may be reported to the care team. The application may also use the day of surgery as a trigger to confirm that postoperative questionnaires (e.g., the Forgotten Knee Score) may be included with the daily task list (shown in 104). The day of surgery may also be used to indicate to the application that changes in the expected range of motion are to be expected when calculating adherence to the assigned exercises and notifying the clinician accordingly. For example, the anticipated degree of lift during a leg lift is higher 80 days post-surgery than 70 days post-surgery.

The sensors on the wearable device may be used for gesture-based controls (e.g. shake first to redo routine, double tap hip to add extra repetitions). In an example, the wearable device may use voice input for rep counting, controlling the app on the mobile device. For example, commands may include, zoom in on the ankle, replay last 15 seconds, etc.

Figure 7A:
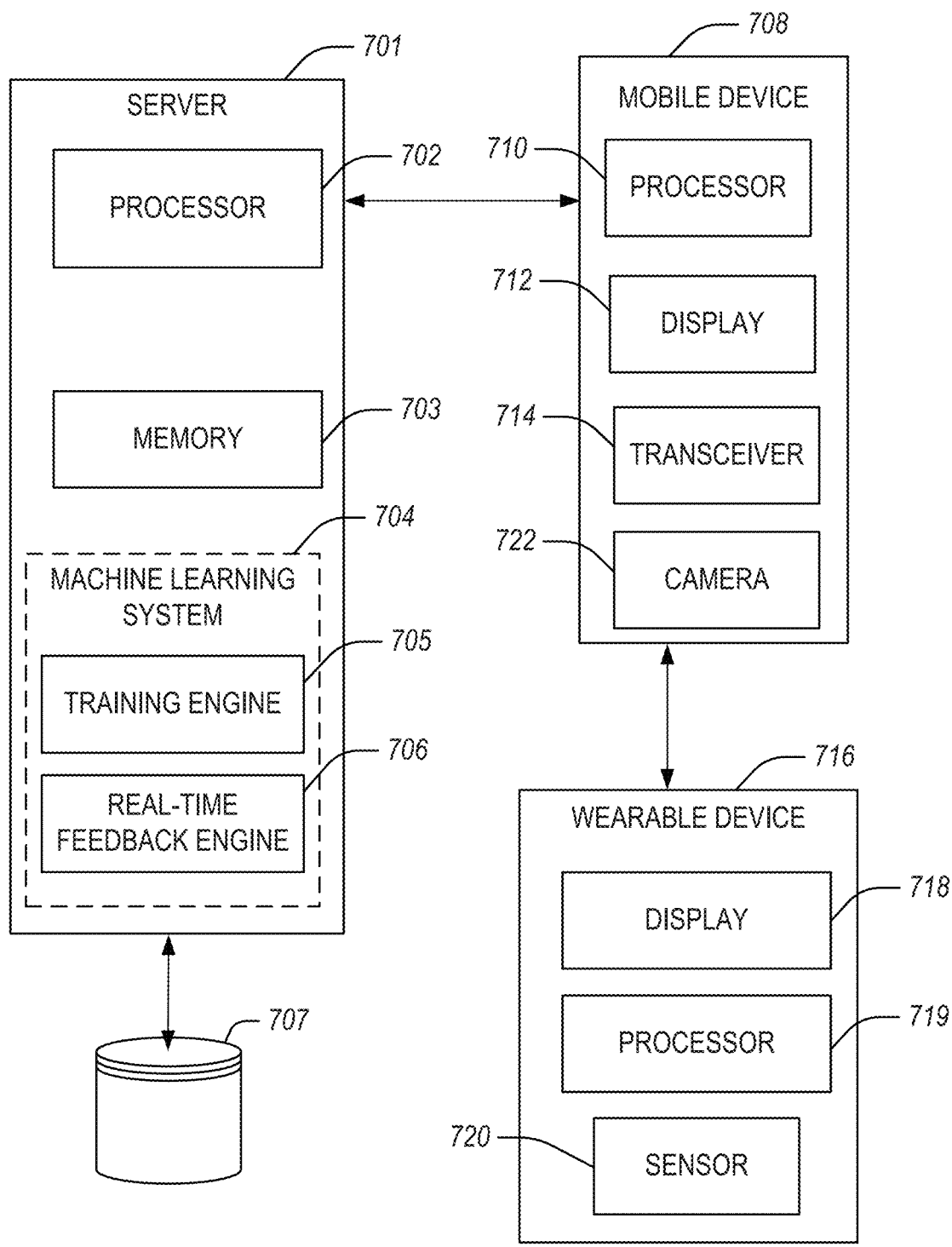
FIG. 7A illustrates a system for presenting and tracking pre and/or post-operative therapy in accordance with some embodiments.

FIG. 7A illustrates a system 700 for presenting and tracking postoperative therapy in accordance with some embodiments. The system 700 includes a server 701 including a processor 702, memory 704, and database 707. The database 707 may include electronic medical records of patients under a surgical care plan. The system 700 includes a mobile device 708 including a processor 710, a display 712, and a transceiver 714. The transceiver 714 may be used to communicate with the server 701 or a wearable device 716. The wearable device 716 may include a display 718, a processor 719, and a sensor 720. The wearable device may include a transceiver for communication with the mobile device 708. In certain examples, the server 701 may also include a machine learning system 704. The machine learning system 704 may include a training engine 705 and a real-time feedback engine 706. In some examples, the machine learning system 701 may learn behaviors from data received from the mobile device 708 collected by the wearable device 716. The machine learning system 701 may react to the collected data through the real-time feedback engine 706, and alter schedule recovery therapy to account to deviations in behavior, improvement in performance, or degradation in performance. In an example, the machine learning system 704 may output information to the mobile device 708 or the database 707.

In an example, the machine learning system 704 may train using the related prior surgical procedures, including, for example, aggregated data detailing outcomes and adherence to recovery therapy plans for past patients undergoing similar surgical procedures. Changes to a therapy plan recommended by the machine learning system 704 may be the result of the real-time feedback engine 706 applying a training set processed through the training engine 705. In an example, the machine learning system 704 may adjust a therapy plan by extrapolating a current patient state to a positive outcome state, resulting a revised therapy plan. The machine learning system 704 may select the recommended change from the plurality of recommended changes, such as based on outcome likelihoods of the plurality of recommended changes.

In an example, the information about related prior surgical procedures may include patient-specific information about a past procedure performed on the patient. In another example, the information about related prior surgical procedures includes demographic-specific information corresponding to the patient. For example, the demographic-specific information may include at least one of patient size (e.g., height, weight, gender, which knee, etc.), surgical procedure type, patient age, or the like.

The training engine 705 may receive adherence data from past patients and correlate outcomes to adherence to create a trained model saved to database 707. Various machine learning techniques may be used to apply weights to inputs, based on training data, to allow for the real-time feedback engine 706 to provide a real-time recommendation or alert when a change or information is identified as potentially relevant to a particular therapy plan event or activity.

The devices and components described in the system 700 may be used to perform the techniques described herein. For example, the mobile device 708 may play a routine on the display 712, playback of which may be controlled by the wearable device 716 (e.g., by receiving a user input on the display 718). The wearable device 716 may count reps, time, or otherwise automatically detect performance of a patient engaged in the routine while wearing the wearable device 716, such as by using the sensor 720, which may include an IMU, a nine-axis sensor, or the like. In an example, the server 701 may store a therapy calendar for postoperative therapy.

In an example, the mobile device 708 may use the display 712 and the processor 710 to perform operations, such as those discussed below related to techniques 800 and 900. For example, the display 712 may present, on a user interface, a therapy calendar, at least one question of a questionnaire, education information, or feedback information/a feedback request. The processor 710 may, in an example, in response to receiving an answer to the at least one question, send a video of an exercise to the display. In an example, the processor 710 may receive a control command from the wearable device, the control command causing an action to be taken by the mobile device related to the exercise. The processor 710 may receive tracking information from the wearable device related to the exercise. The processor 710 may determine a number of repetitions or a duration of the exercise from the tracking information.

The processor may automatically modify the therapy calendar in response to determining the number of repetitions or the duration, or based on the response to the at least one question, a user input during presentation of the education information, based on the control command, or the like. In an example, the therapy calendar may be automatically modified by the processor 710 based on feedback information received from the user related to the exercise. The processor 710 may send to the display for presentation on the user interface of the display, the modified therapy calendar.

The mobile device 708 may include a camera 722, for example to record video of a user performing an exercise. The video may be used to determine a number of repetitions or a duration. The wearable device 708 may use the sensor 724, for example to record information of a user performing an exercise. The information may be used to determine a number of repetitions or a duration. For example, the tracking information described above may include the information recorded by the sensor 724.

The wearable device 716 may present, on a user interface of the display 718, a therapy calendar. The wearable device 716 may include a processor to send a control command to the mobile device, the control command causing an action to be taken by the mobile device related to the exercise. The sensor 718 may be used to track actions taken by a user. In an example, the processor of the wearable device 716 may receive, from the sensor 718, tracking information related to the exercise.

The processor of the wearable device 716 may determine a number of repetitions or a duration of the exercise from the tracking information or send the tracking information to the mobile device 708 to determine the number of repetitions or the duration, which may then be sent back to the wearable device 716. The processor of the wearable device 716 may automatically modify the therapy calendar in response to determining or receiving the number of repetitions or the duration, or the wearable device 716 may receive the modified therapy calendar from the mobile device 708. In an example, the display 718 of the wearable device 716 may present the modified therapy calendar on the user interface.

The wearable device 716 may send the modified therapy calendar to the mobile device 708 for display. The display 718 may present on the user interface, at least one question of a questionnaire, and the wearable device 716 may receive, via a user selection on the user interface, an answer to the at least one question. In an example, in response to receiving the answer to the at least one question, the display 718 may display a video of the exercise on the user interface. In an example, in response to receiving the answer to the at least one question, the wearable device 716 may send an indication to the mobile device 708 to display a video of the exercise (e.g., on the display 712).

Figure 7B:
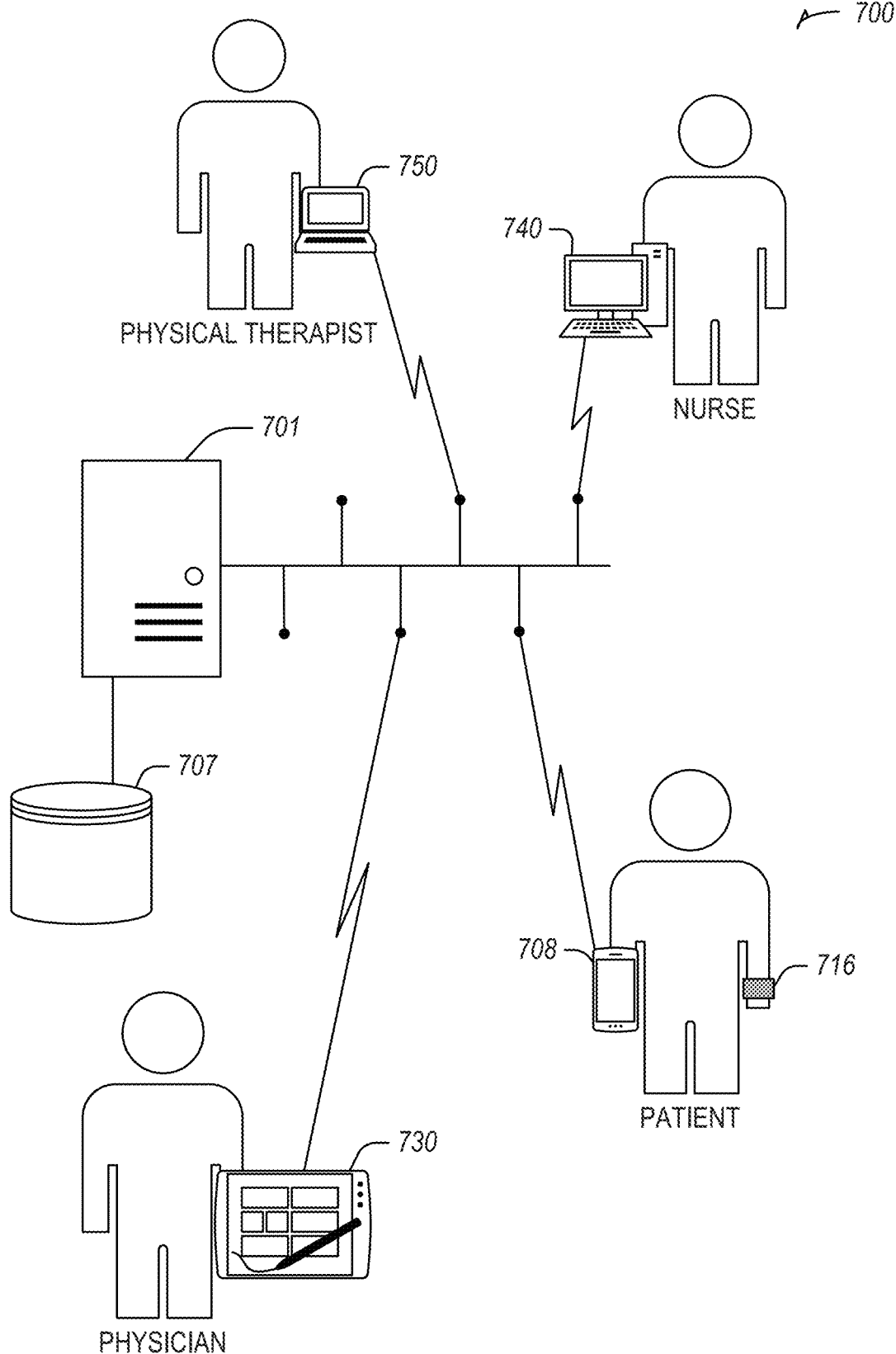
FIG. 7B illustrates a system for delivering pre and/or post-operative content and tracking related activities in accordance with some embodiments.

FIG. 7B illustrates a system 700 for delivering pre and/or post-operative content and tracking related activities in accordance with some embodiments. The system 700 illustrated in FIG. 7B includes the server 701, database 707, mobile device 708, and wearable 716 discussed above. The components discussed in reference to FIG. 7A may be viewed as the patient side of the system, while FIG. 7B brings in the clinician side of the system 700. In this example, the clinician side may include a tablet device 730 operated by a physician, a desktop personal computer, device 740, operated by a nurse (or similar staff), and a laptop 750 operated by a physical therapist who may be part of an extended care team. The example illustrated in FIG. 7B depicts representative members of a care team using representative client devices, other example may include other members of a care team using other types of computing devices to interact with the patient and monitor adherence to a therapy plan. In this example, the tablet 730, device 740 and laptop 750 may all communicate with the server 701 via a network, such as the Internet.

Each member of the care team may interact with the therapy plan by monitoring adherence, updating the therapy calendar, changing a particular activity based on feedback received from the patient via the mobile device 708 and/or wearable 716. For example, the physical therapist may access an activity log generated by the wearable 716 detailing how well the patient is able to perform certain recovery activities. Based on a review of the activity log, the physical therapist may add repetitions, suggest alternative activities, or notify the nurse of physician that follow up with the patient may be needed. The physician via the tablet device 730 may review an aggregation of questionnaire responses to ensure the patient's recovery is trending in the right direction. Pre-operatively, the physician or nurse may provide education materials for review by the patient.

Figure 8:
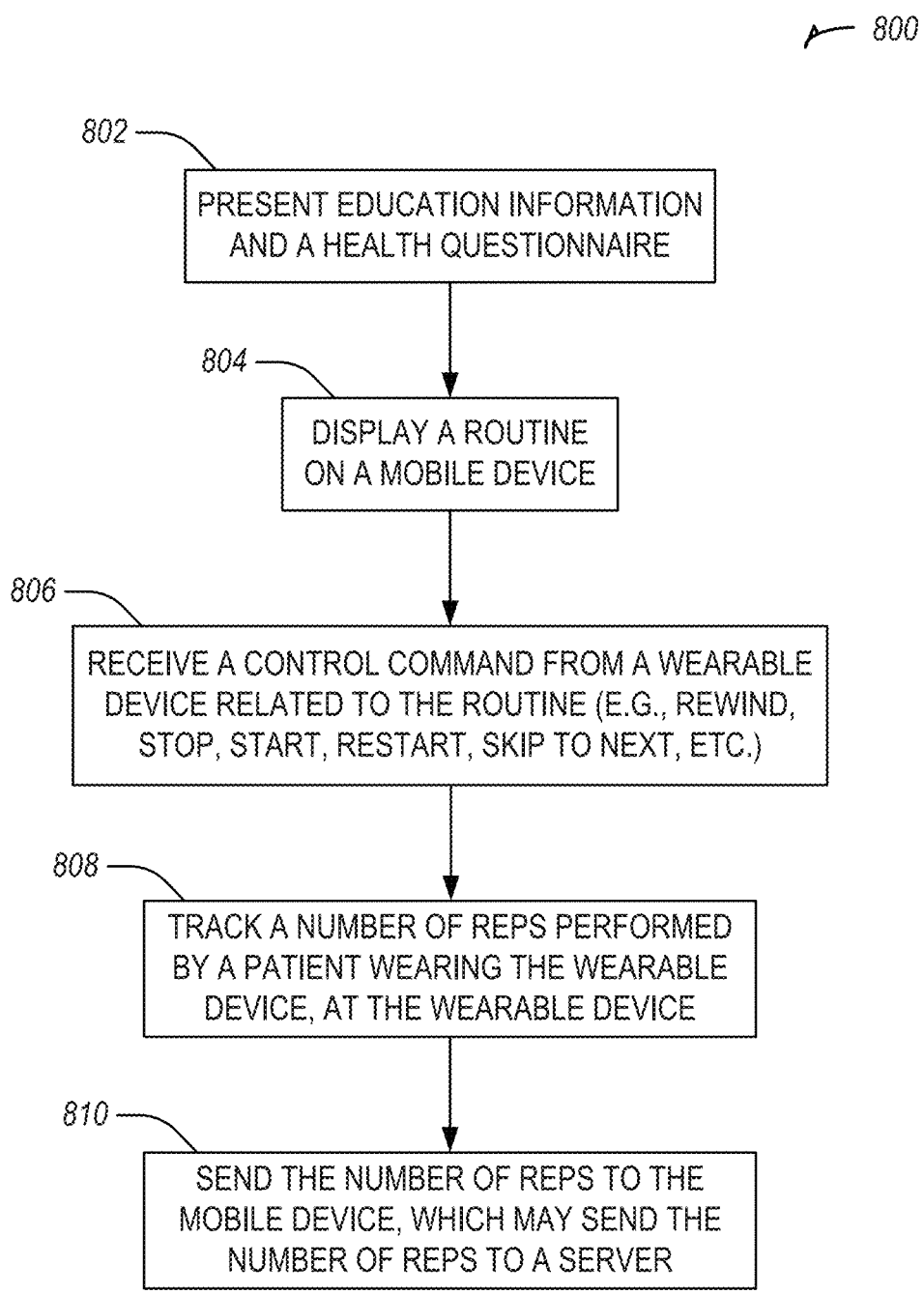
FIG. 8 illustrates a flow chart showing a technique for presenting and tracking post-operative therapy in accordance with some embodiments.

FIG. 8 illustrates a flow chart showing a technique 800 for presenting and tracking pre- or postoperative therapy in accordance with some embodiments. The technique 800 may include operations 802-810. Operation 802 includes presenting education information and a health questionnaire, such as on a mobile device, which may be controlled by a wearable device. Operation 804 includes displaying a routine on a mobile device. The routine includes a therapeutic movement, such as a stretch, lifting a weight, lifting without a weight, extension, flexion, side-to-side movement, isolated movement of joints, movement of joints together, etc. The routine may be displayed on the mobile device and controlled by the wearable device. Operation 806 includes receiving a control command from a wearable device related to the routine (e.g., rewind, stop, start, pause, restart, skip to next, etc.). The control command may remotely control playback of the routine on the mobile device. Operation 808 includes tracking a number of reps performed by a patient wearing the wearable device, at the wearable device. The tracking may include using an IMU, a nine-axis sensor, etc.

For example, the tracking may automatically count a number of reps, it may disqualify some movement as not counting as a rep, etc. In another example, the wearable device may be used to automatically count time during a routine, such as an amount of time a stretch is held. Operation 810 includes sending the number of reps (or the time, etc.) to the mobile device, which may send the number of reps to a server. The server may update a surgeon, physical therapist, other doctor, etc., such as on the progress of the patient wearing the wearable device.

Figure 9:
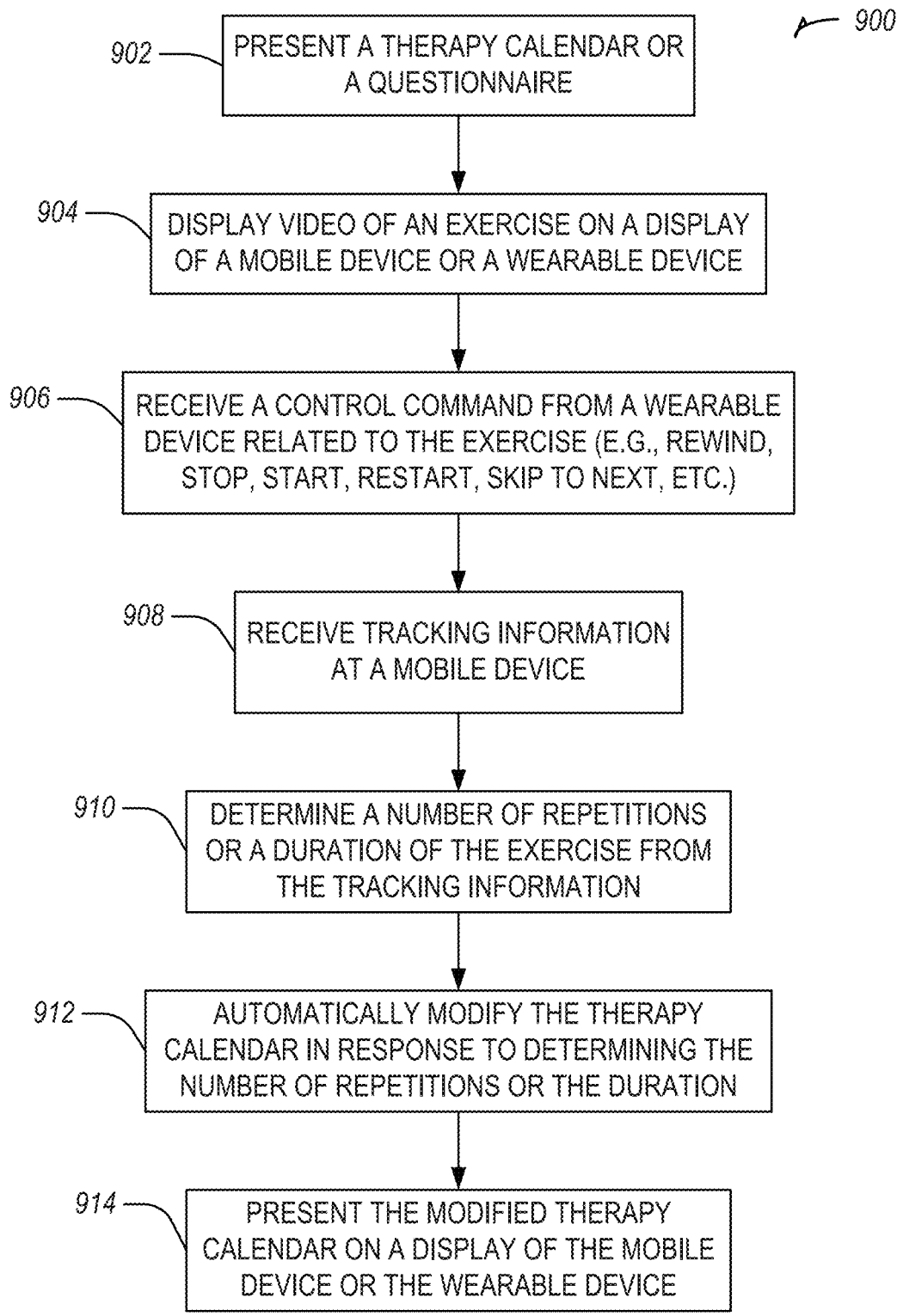
FIG. 9 illustrates a flow chart showing a technique for updating a therapy calendar based on actions taken by a user, such as recorded by a mobile device or a wearable device in accordance with some embodiments.

FIG. 9 illustrates a flow chart showing a technique 900 for updating a therapy calendar based on actions taken by a user, such as recorded by a mobile device or a wearable device in accordance with some embodiments. The technique 900 includes an operation 902 to present a therapy calendar, education information, or a questionnaire, for example on a user interface of a display, such as a display of a mobile device or a wearable device. The technique 900 includes an operation 904 to display video of an exercise on a display of a mobile device or a wearable device, such as in response to receiving an answer to the at least one question.

The technique 900 includes an operation 906 to receive a control command from a wearable device related to the exercise (e.g., rewind, stop, start, restart, skip to next, etc.), for example, the control command may cause an action to be taken by the mobile device related to the exercise. The technique 900 includes an operation 908 to receive tracking information at the mobile device, for example from the wearable device related to the exercise.

The technique 900 includes an operation 910 to determine a number of repetitions or a duration of the exercise from the tracking information, for example at the mobile device or the wearable device using a processor. In an example, the number of repetitions or the duration may be determined at the mobile device using a processor based on tracking information sent from the wearable device. In another example, the tracking information may include the number of repetitions or the duration (e.g., as determined by a processor of the wearable device) when sent to the mobile device from the wearable device.

The technique 900 includes an operation 912 to automatically modify the therapy calendar in response to determining the number of repetitions or the duration. In an example, operation 912 may include automatically modifying the therapy calendar based on a user input during presentation of education information, based on an answer to at least one question of the questionnaire, or based on the control command.

The technique 900 includes an operation 914 to present the modified therapy calendar on a display of the mobile device or the wearable device. The technique 900 may include an operation to send the modified therapy calendar to the wearable device from the mobile device (or vice versa) for display. The technique 900 may include an operation to present, such as on a user interface of a display of the mobile device or the wearable device, a feedback question to a user. This operation may include receiving feedback information from the user related to the exercise. In an example, the therapy calendar may be automatically modified based on the feedback information from the user.

Figure 10:
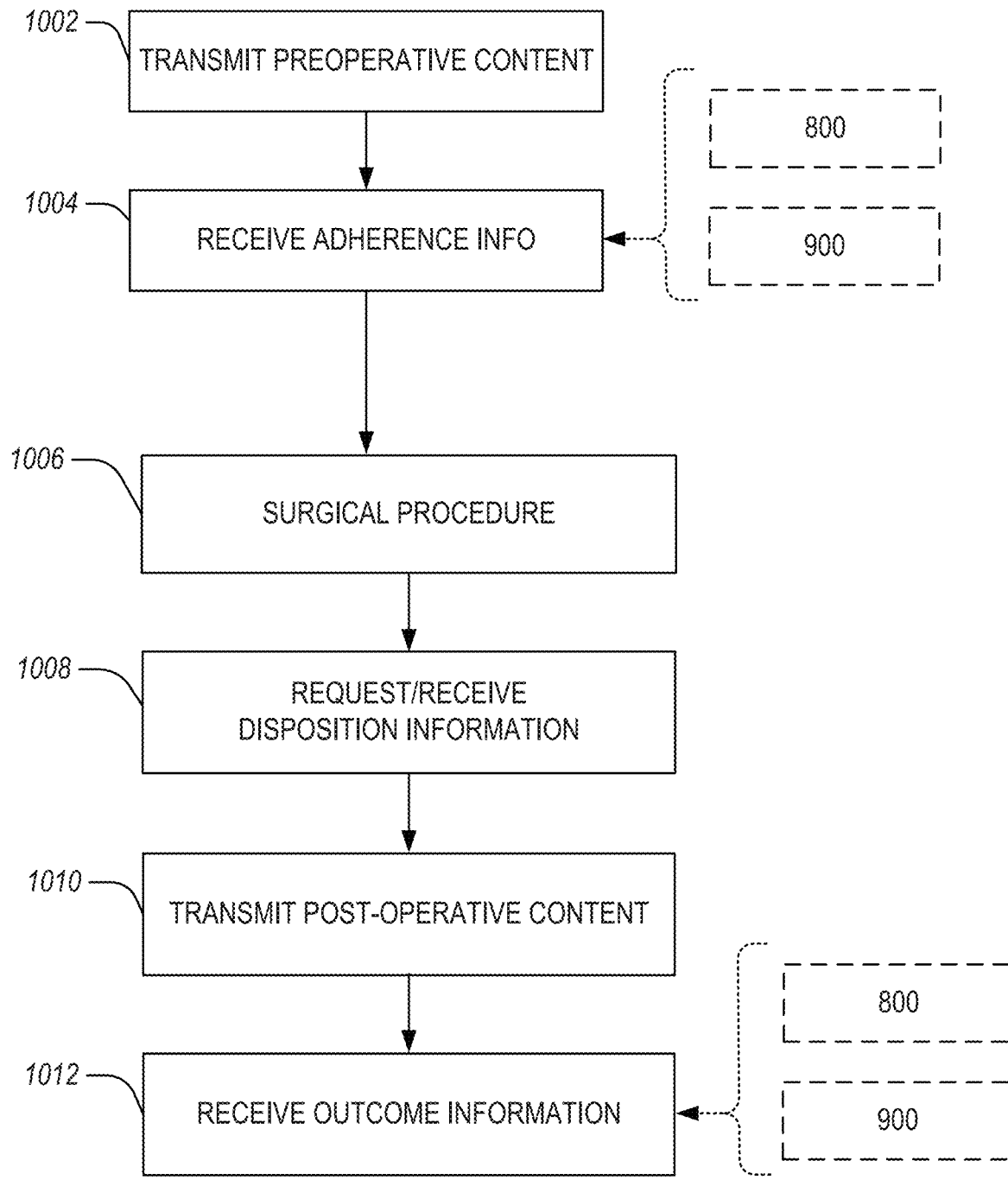
FIG. 10 illustrates a flow chart showing a technique for delivering pre and/or post-operative educational content and collecting tracked data associated with a procedure in accordance with some embodiments.

FIG. 10 is a flow chart showing a technique 1000 for delivering pre and/or post-operative educational content, surgical care plan, and collecting tracked data associated with a procedure in accordance with some embodiments. In this example, the technique 1000 may include operations such as transmitting preoperative content at 1002, receiving adherence information at 1004, conducting the surgical procedure at 1006, requesting and/or receiving disposition information regarding the surgical procedure at 1008, transmitting post-operative content at 1010, and receiving outcome information at 1012. As discussed below in detail, the technique 1000 may be performed primarily by server 701 or components of system 700. The operation involving the conducting the surgical procedure is included in the discussion of technique 1000 to provide a complete picture of the environment and provide a clear indication of pre-operative operations versus post-operative activities. Technique 1000 may be considered complete without inclusion of the surgical procedure 1006. However, understanding when the surgical procedure 1006 occurs is useful in gaining a complete understanding of technique 1000.

The technique 1000 may begin at 1002 with a member of the care team, such as a nurse via device 740, transmitting pre-operative content to a patient. The pre-operative content may include materials to educate the patient on the upcoming procedure as well as a pre-operative therapy plan. The pre-operative therapy plan may include exercises or other actions, such as a regiment of medications, that the patient should adhere to in the days leading up to the procedure. At 1004, the technique 1000 may continue with the server 701 receiving adherence information, which may be generated by the wearable 716 and transmitted to the server via the mobile device 708. As depicted, operation 1004 may involve receiving adherence information in accordance with aspects of techniques 800 and 900 discussed above. The techniques 800 and 900 are discussed in terms of post-operative therapy, but are similar applicable to pre-operative care plans. Just like in a post-operative scenario, a lack of adherence to the pre-operative plan may result in deviations to the plan and/or postponement of the procedure.

In this example, the technique 1000 continues at 1006 with the surgical procedure being conducted by parts of the care team, including the physician. At 1008, the post-operative portion of technique 1000 begins with the server 701 requesting and receiving disposition information from the patient. The patient, via mobile device 708, may provide responses to a questionnaire to provide objective feedback regarding the surgical procedure. At 1010, the technique 1000 continues with the server 701 transmitting post-operative content to the patient. As discussed herein, the post-operative content may include additional educational materials and a therapy calendar, among other things. At 1012, the technique 1000 may conclude with the server 701 receiving outcome information, such as adherence information and/or questionnaire responses. Again, operation 1012 may include receiving information generated in techniques 800 and/or 900, as discussed above.

Figure 11:
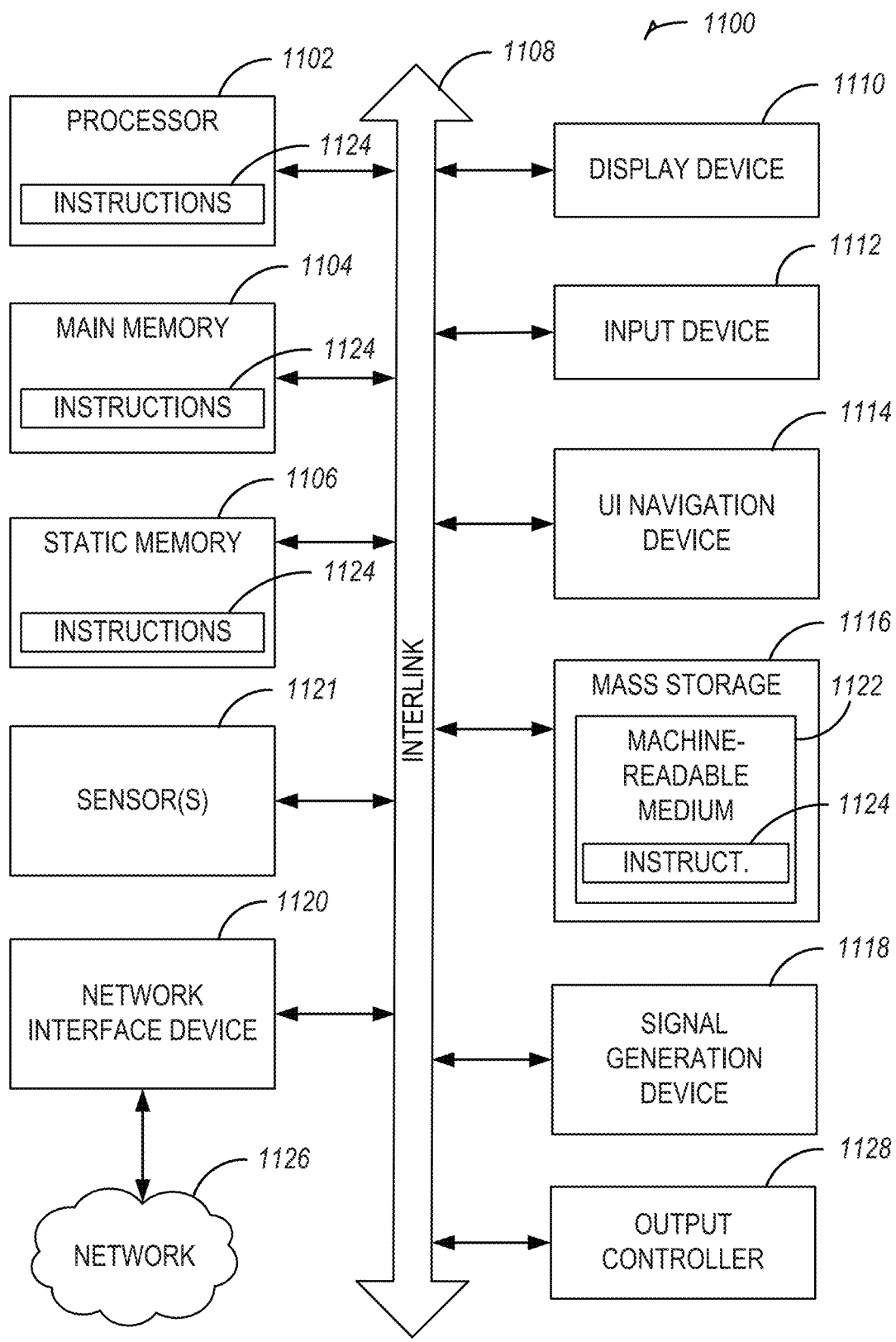
FIG. 11 illustrates generally an example of a block diagram of a machine upon which any one or more of the techniques discussed herein may perform in accordance with some embodiments.

FIG. 11 illustrates generally an example of a block diagram of a machine 1100 upon which any one or more of the techniques (e.g., methodologies) discussed herein may perform in accordance with some embodiments. In alternative embodiments, the machine 1100 may operate as a standalone device or may be connected (e.g., networked) to other machines. In a networked deployment, the machine 1100 may operate in the capacity of a server machine, a client machine, or both in server-client network environments. The machine 1100 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 1100 may include a hardware processor 1102 (e.g., a central processing unit (CPU), a graphics processing unit (GPU), a hardware processor core, or any combination thereof), a main memory 1104 and a static memory 1106, some or all of which may communicate with each other via an interlink (e.g., bus) 1108. The machine 1100 may further include a display unit 1110, an alphanumeric input device 1112 (e.g., a keyboard), and a user interface (UI) navigation device 1114 (e.g., a mouse). In an example, the display unit 1110, alphanumeric input device 1112 and UI navigation device 1114 may be a touch screen display. The display unit 1110 may include goggles, glasses, or other AR or VR display components. For example, the display unit may be worn on a head of a user and may provide a heads-up-display to the user. The alphanumeric input device 1112 may include a virtual keyboard (e.g., a keyboard displayed virtually in a VR or AR setting.

The machine 1100 may additionally include a storage device (e.g., drive unit) 1116, a signal generation device 1118 (e.g., a speaker), a network interface device 1120, and one or more sensors 1021, such as a global positioning system (GPS) sensor, compass, accelerometer, or other sensor. The machine 1100 may include an output controller 1128, such as a serial (e.g., universal serial bus (USB), parallel, or other wired or wireless (e.g., infrared (IR), near field communication (NFC), etc.) connection to communicate or control one or more peripheral devices.

The storage device 1116 may include a machine readable medium 1122 that is non-transitory on which is stored one or more sets of data structures or instructions 1124 (e.g., software) embodying or utilized by any one or more of the techniques or functions described herein. The instructions 1124 may also reside, completely or at least partially, within the main memory 1104, within static memory 1106, or within the hardware processor 1102 during execution thereof by the machine 1100. In an example, one or any combination of the hardware processor 1102, the main memory 1104, the static memory 1106, or the storage device 1116 may constitute machine readable media.

While the machine readable medium 1122 is illustrated as a single medium, the term "machine readable medium" may include a single medium or multiple media (e.g., a centralized or distributed database, or associated caches and servers) configured to store the one or more instructions 1124.

The term "machine readable medium" may include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1124 may further be transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 1120 may include one or more physical jacks (e.g., Ethernet, coaxial, or phone jacks) or one or more antennas to connect to the communications network 1126. In an example, the network interface device 1120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

Various Notes & Examples

Each of these non-limiting examples may stand on its own, or may be combined in various permutations or combinations with one or more of the other examples.

Example 1 is a mobile device communicatively coupled to a wearable device, the mobile device comprising: a display device configured to: present, on a user interface, a therapy calendar; and present, on the user interface, at least one question of a questionnaire; and processing circuitry configured to: in response to receiving an answer to the at least one question, send a video of an exercise to the display; receive a control command from the wearable device, the control command causing an action to be taken by the mobile device related to the exercise; receive tracking information from the wearable device related to the exercise; determine a number of repetitions or a duration of the exercise from the tracking information; automatically modify the therapy calendar in response to determining the number of repetitions or the duration; and send to the display for presentation on the user interface of the display, the modified therapy calendar.

In Example 2, the subject matter of Example 1 includes, wherein the display is further configured to present, on the user interface, education information.

In Example 3, the subject matter of Example 2 includes, wherein to automatically modify the therapy calendar, the processing circuitry is further configured to automatically modify the therapy calendar based on a user input during presentation of the education information.

In Example 4, the subject matter of Examples 1-3 includes, wherein the display is further configured to present, on the user interface, a feedback question to a user, and wherein the processing circuitry is further configured to: receive feedback information from the user related to the exercise; and automatically modify the therapy calendar based on the feedback information from the user.

In Example 5, the subject matter of Examples 1-4 includes, wherein to automatically modify the therapy calendar, the processing circuitry is further configured to automatically modify the therapy calendar based on the control command.

In Example 6, the subject matter of Examples 1-5 includes, wherein to automatically modify the therapy calendar, the processing circuitry is further configured to automatically modify the therapy calendar based on the answer to the at least one question.

In Example 7, the subject matter of Examples 1-6 includes, wherein the mobile device further comprises a camera, the camera to record video of a user performing the exercise.

In Example 8, the subject matter of Examples 1-7 includes, wherein the tracking information includes information recorded by a sensor of the wearable device.

In Example 9, the subject matter of Examples 1-8 includes, wherein the processing circuitry is further to send the modified therapy calendar to the wearable device for display.

Example 10 is a method comprising: presenting, on a user interface of a display of a mobile device, a therapy calendar; presenting, on the user interface of the display, at least one question of a questionnaire; in response to receiving an answer to the at least one question, displaying a video of an exercise on the display; receiving, at a processor of the mobile device, a control command from a wearable device communicatively coupled to the mobile device, the control command causing an action to be taken by the mobile device related to the exercise; receiving, at the processor, tracking information from the wearable device related to the exercise; determining, at the processor, a number of repetitions or a duration of the exercise from the tracking information; automatically modifying, using the processor, the therapy calendar in response to determining the number of repetitions or the duration; and presenting the modified therapy calendar on the user interface of the display.

In Example 11, the subject matter of Example 10 includes, presenting, on the user interface of the mobile device, education information.

In Example 12, the subject matter of Example 11 includes, wherein automatically modifying the therapy calendar includes automatically modifying the therapy calendar based on a user input during presentation of the education information.

In Example 13, the subject matter of Examples 10-12 includes, presenting, on the user interface of the display, a feedback question to a user; receiving feedback information from the user related to the exercise; and automatically modifying the therapy calendar based on the feedback information from the user.

In Example 14, the subject matter of Examples 10-13 includes, wherein automatically modifying the therapy calendar includes automatically modifying the therapy calendar based on the control command or the answer to the at least one question.

In Example 15, the subject matter of Examples 10-14 includes, sending the modified therapy calendar to the wearable device for display.

Example 16 is a wearable device communicatively coupled to a mobile device, the wearable device comprising: at least one sensor configured to track actions taken by a user; a display; and processing circuitry configured to: present, on a user interface of the display, a therapy calendar; send a control command to the mobile device, the control command causing an action to be taken by the mobile device related to the exercise; receive, from the at least one sensor, tracking information related to the exercise; determine a number of repetitions or a duration of the exercise from the tracking information; automatically modify the therapy calendar in response to determining the number of repetitions or the duration; and present the modified therapy calendar on the user interface of the display.

In Example 17, the subject matter of Example 16 includes, wherein the processing circuitry is further configured to send the modified therapy calendar to the mobile device for display.

In Example 18, the subject matter of Examples 16-17 includes, wherein the display is further to present, on the user interface, at least one question of a questionnaire, and wherein the processing circuitry is further configured to receive, via a user selection on the user interface, an answer to the at least one question.

In Example 19, the subject matter of Example 18 includes, wherein in response to receiving the answer to the at least one question, the display is further configured to display a video of the exercise on the user interface.

In Example 20, the subject matter of Examples 18-19 includes, wherein in response to receiving the answer to the at least one question, the processing circuitry is further configured to send an indication to the mobile device to display a video of the exercise.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A mobile device communicatively coupled to a wearable device worn by a user, the mobile device comprising:
a memory to store a plurality of postoperative therapy plan calendar entries;
a display device configured to:
present, on a user interface, a therapy calendar, the therapy calendar displaying at least a portion of the plurality of postoperative therapy plan calendar entries; and
present, on the user interface, at least one question of a questionnaire; and
processing circuitry configured to:
in response to receiving an answer to the at least one question, send a video of a postoperative therapy plan exercise to the display device;
receive accelerometer sensor data generated by an accelerometer sensor of a wearable device worn on a wrist of the user, the accelerometer sensor data generated by the accelerometer sensor in response to a predetermined gesture-based movement of the wearable device while the user is performing the postoperative therapy plan exercise;
identify a predetermined repetitive motion gesture based on the accelerometer sensor data;
generate a modified therapy plan exercise at the mobile device based on the postoperative therapy plan exercise and the predetermined repetitive motion gesture, wherein generating the modified therapy plan exercise is initiated in response to the user tapping a user body part while the user is wearing the wearable device on the wrist of the user to induce motion in the accelerometer sensor;
display the modified therapy plan exercise on the mobile device;
receive tracking information from the wearable device related to a user performance of the modified therapy plan exercise;
determine an exercise adherence metric from the tracking information, the exercise adherence metric including at least one of a number of repetitions, a duration, or a range of motion;
send the exercise adherence metric to a server;
receive an updated therapy calendar entry from the server including a modification to a future adherence metric on the therapy calendar;
automatically modify the plurality of postoperative therapy plan calendar entries using the updated therapy calendar entry, wherein the modification is based on a server determination that the exercise adherence metric is below an expected adherence metric, wherein the expected adherence metric is increased based on an increasing number of days post-surgery; and
send to the display device for presentation on the user interface, the updated therapy calendar entry.

2. The mobile device of claim 1, wherein the display device is further configured to present, on the user interface, education information.

3. The mobile device of claim 2, wherein to automatically modify the therapy calendar, the processing circuitry is further configured to automatically modify the therapy calendar based on a user input during presentation of the education information.

4. The mobile device of claim 1, wherein the display device is further configured to present, on the user interface, a feedback question to a user, and wherein the processing circuitry is further configured to:
receive feedback information from the user related to the postoperative therapy plan exercise; and
automatically modify the therapy calendar based on the feedback information from the user.

5. The mobile device of claim 1, wherein to automatically modify the therapy calendar, the processing circuitry is further configured to automatically modify the therapy calendar based on the accelerometer sensor data.

6. The mobile device of claim 1, wherein to automatically modify the therapy calendar, the processing circuitry is further configured to automatically modify the therapy calendar based on the answer to the at least one question.

7. The mobile device of claim 1, wherein the mobile device further comprises a camera, the camera to record video of a user performing the postoperative therapy plan exercise.

8. The mobile device of claim 1, wherein generating the modified therapy plan exercise at the mobile device is based on the postoperative therapy plan exercise.

9. The mobile device of claim 1, wherein the processing circuitry is further to send the updated therapy calendar entry to the wearable device for display.

10. A method comprising:
retrieving a plurality of postoperative therapy plan calendar entries from a memory of a mobile device;
presenting, on a user interface of a display of the mobile device, a therapy calendar, the therapy calendar displaying at least a portion of the plurality of postoperative therapy plan calendar entries;
presenting, on the user interface of the display, at least one question of a questionnaire;
in response to receiving an answer to the at least one question, displaying a video of a postoperative therapy plan exercise to the display;
receiving, at a processor of the mobile device, accelerometer sensor data generated by an accelerometer sensor of a wearable device worn on a wrist of a user and communicatively coupled to the mobile device, the accelerometer sensor data generated by the accelerometer sensor in response to a predetermined gesture-based movement of the wearable device while the user is performing the postoperative therapy plan exercise;
identifying a predetermined repetitive motion gesture based on the accelerometer sensor data;
generating a modified therapy plan exercise at the mobile device based on the postoperative therapy plan exercise and the predetermined repetitive motion gesture, wherein generating the modified therapy plan exercise is initiated in response to the user tapping a user body part while the user is wearing the wearable device on the wrist of the user to induce motion in the accelerometer sensor;
displaying the modified therapy plan exercise on the mobile device;
receiving, at the processor, tracking information from the wearable device related to a user performance of the modified therapy plan exercise;
determining, at the processor, an exercise adherence metric from the tracking information, the exercise adherence metric including at least one of a number of repetitions, a duration, or a range of motion;
sending the exercise adherence metric to a server;
receiving an updated therapy calendar entry from the server including a modification to a future adherence metric on the therapy calendar;
automatically modifying, using the processor, the plurality of postoperative therapy plan calendar entries using the updated therapy calendar entry, wherein the modification is based on a server determination that the exercise adherence metric is below an expected adherence metric, wherein the expected adherence metric is increased based on an increasing number of days post-surgery; and
presenting the updated therapy calendar entry on the user interface of the display.

11. The method of claim 10, further comprising presenting, on the user interface of the mobile device, education information.

12. The method of claim 11, wherein automatically modifying the therapy calendar includes automatically modifying the therapy calendar based on a user input during presentation of the education information.

13. The method of claim 10, further comprising:
presenting, on the user interface of the display, a feedback question to a user;
receiving feedback information from the user related to the postoperative therapy plan exercise; and
automatically modifying the therapy calendar based on the feedback information from the user.

14. The method of claim 10, wherein automatically modifying the therapy calendar includes automatically modifying the therapy calendar based on the accelerometer sensor data or the answer to the at least one question.

15. The method of claim 10, further comprising sending the updated therapy calendar entry to the wearable device for display.

16. A wearable device worn by a user communicatively coupled to a mobile device, the wearable device comprising:
a memory to store a plurality of postoperative therapy plan calendar entries;
at least one sensor configured to track actions taken by the user;
a display; and
processing circuitry configured to:
present, on a user interface of the display, a therapy calendar, the therapy calendar displaying at least a portion of the plurality of postoperative therapy plan calendar entries;
send accelerometer sensor data generated by an accelerometer sensor of a wearable device worn on a wrist of the user to the mobile device, the accelerometer sensor data generated by the accelerometer sensor in response to a predetermined gesture-based movement of the wearable device;
identify a predetermined repetitive motion gesture based on the accelerometer sensor data;
generate a modified therapy plan exercise at the mobile device based on a postoperative therapy plan exercise and the predetermined repetitive motion gesture, wherein generating the modified therapy plan exercise is initiated in response to the user tapping a user body part while the user is wearing the wearable device on the wrist of the user to induce motion in the accelerometer sensor;
display the modified therapy plan exercise on the mobile device;
receive, from the at least one sensor, tracking information related to a user performance of the modified therapy plan exercise;
determine an exercise adherence metric from the tracking information, the exercise adherence metric including at least one of a number of repetitions, a duration, or a range of motion;
send the exercise adherence metric to the mobile device;
receive an updated therapy calendar entry from the mobile device including a modification to a future adherence metric on the therapy calendar;
automatically modify the plurality of postoperative therapy plan calendar entries using the updated therapy calendar entry, wherein the modification is based on a determination at the mobile device that the exercise adherence metric is below an expected adherence metric, wherein the expected adherence metric is increased based on an increasing number of days post-surgery; and
present the updated therapy calendar entry on the user interface of the display.

17. The wearable device of claim 16, wherein the processing circuitry is further configured to send the updated therapy calendar entry to the mobile device for display.

18. The wearable device of claim 16, wherein the display is further to present, on the user interface, at least one question of a questionnaire, and wherein the processing circuitry is further configured to receive, via a user selection on the user interface, an answer to the at least one question.

19. The wearable device of claim 18, wherein in response to receiving the answer to the at least one question, the display is further configured to display the modified therapy plan exercise on the user interface.

20. The wearable device of claim 18, wherein in response to receiving the answer to the at least one question, the processing circuitry is further configured to send an indication to the mobile device to display a video of the postoperative therapy plan exercise.

* * * * *